United States Patent
Zhao et al.

(10) Patent No.: US 8,114,638 B2
(45) Date of Patent: Feb. 14, 2012

(54) **ARABINITOL DEHYDROGENASE FROM *NEUROSPORA CRASSA***

(75) Inventors: Huimin Zhao, Champaign, IL (US); Ryan Sullivan, Urbana, IL (US)

(73) Assignees: The Board of Trustees of the University of Illinois, Urbana, IL (US); Biotechnology Research and Development Corporation, Peoria, IL (US)

( * ) Notice: Subject to any disclaimer, the term of this patent is extended or adjusted under 35 U.S.C. 154(b) by 0 days.

(21) Appl. No.: 12/984,016

(22) Filed: Jan. 4, 2011

(65) Prior Publication Data

US 2011/0165631 A1 Jul. 7, 2011

Related U.S. Application Data

(62) Division of application No. 12/235,253, filed on Sep. 22, 2008, now Pat. No. 7,892,804.

(60) Provisional application No. 60/975,023, filed on Sep. 25, 2007.

(51) Int. Cl.
C12P 19/02 (2006.01)
C12N 9/00 (2006.01)
C12N 9/02 (2006.01)
C12N 9/04 (2006.01)
C12N 1/20 (2006.01)
C12N 15/00 (2006.01)
C07H 21/04 (2006.01)

(52) U.S. Cl. ........ 435/105; 435/183; 435/189; 435/190; 435/252.3; 435/320.1; 536/23.2

(58) Field of Classification Search .................. None
See application file for complete search history.

(56) References Cited

U.S. PATENT DOCUMENTS

| | | | |
|---|---|---|---|
| 5,643,758 | A | 7/1997 | Guan et al. |
| 6,582,944 | B1 | 6/2003 | Hallborn et al. |
| 7,381,553 | B2 | 6/2008 | Zhao et al. |
| 2007/0128706 | A1 | 6/2007 | Gorwa-Grauslund et al. |

OTHER PUBLICATIONS

Accession Q7S109. Dec. 15, 2003.
Becker et al., "A Modified *Saccharomyces cerevisiae* Strain That Consumes L-Arabinose and Produces Ethanol," *Applied and Environmental Microbiology*, 67 (7): 4144-4150 (2003).
Database UniProt (2004): "Hypothetical protein (Xylose reductase)," Database Accession No. Q7SD67, (Abstract).
Database EMBL (2000): "*Aspergilus niger* D-xylose reductase (xyrA)gene, complete cds," Database Accession No. XP002360472, (Abstract).
Hasper et al., "The *Aspergillus niger* transcriptional activator XINR, which is involved in the degradation of the polysaccharides xylan and cellulose, also regulates D-xylose reductase gene expression," *Molecular Microbiology*, 36 (1): 193-200 (2000).
Hynes et al., "The *Neurospora crassa* genome opens up the world of filamentous fungi," *Genome Biology*, 4 (217): 217.1-217.4 (2003).
Ikemi et al., "Sorbitol Production in Charged Membrane Bioreactor with Coenzyme Regeneration System: I. Selective Retainment of NADP(H) in a Continuous Reaction," *Biotechnology and Bioengineering*, 36: 149-154 (1990).
Nidetzky et al., "Continuous Enzymatic Production of Xylitol with Simultaneous Coenzyme Regeneration in a Charged Membrane Reactor," *Biotechnology and Bioengineering*, 52: 387-396 (1996).
Rawat et al., "Purification, kinetic characterization and involvement of tryptophan residue at the NADPH binding site of xylose reductase from *Neurospora crassa*," *Biochimica et Biophysica Acta*, 1293: 222-230 (1996).
Rawat et al., "Conformation and microenvironment of the active site of xylose reductase inferred by fluorescent chemoaffinity labeling," *Eur. J. Biochem.*, 246: 344-349 (1997).
Rawat et al., "Site and Significance of Cysteine Residues in Xylose Reductase from *Neurospora crassa* as Deduced by Fluorescence Studies," *Biochemical and Biophysical Research Communications*, 239: 789-793 (1997).
Richard et al., "Cloning and Expression of a Fungal L-Arabinitol 4-Dehydrogenase Gene," *The Journal of Biological Chemistry*, 276 (44): 40631-40637 (2001).
Verho at al., "Engineering Redox Cofactor Regeneration for Improved Pentose Fermentation in *Saccharomces cerevisiae*," *Applied and Environmental Microbiology*, 39 (10): 5892-5897 (2003).
Watanabe et al., "Complete Reversal of Coenzyme Specificity of Xylitol Dehydrogenase and Increase of Thermostability by the Introduction of Structural Zinc," *The Journal of Biological Chemistry*, 280 (11): 10340-10349 (2005).
Woodyer at al., "Heterologous Expression, Purification, and Characterization of a Highly Active Xylose Reductase from *Neurospora crassa*," *Applied and Environmental Microbiology*, 71 (3): 1642-1647 (2005).
Zhao et al., "The Production and Properties of a New Xylose Reductase from Fungus," *Applied Biochemistry and Biotechnology*, 70-72: 405-414 (1998).

*Primary Examiner* — Christian Fronda
(74) *Attorney, Agent, or Firm* — Barnes & Thornburg LLP; Alice O. Martin

(57) ABSTRACT

Stable and active arabinitol dehydrogenases (LAD) from *Neurospora crassa* and mutants thereof are disclosed. Arabinitol dehydrogenases are useful in the production of xylitol and ethanol from an arabinose containing substrate. Recombinant and heterologously expressed arabinitol dehydrogenases are useful in converting biomass into biofuels and other industrial food products.

4 Claims, 8 Drawing Sheets

```
Neurospora crassa      MASSAS--------------RTNIGVFTNPQRDLWISEASPSLESVQKGEE
Hypocrea jecorina      MSPSAVDDAPKATGAAISVKPNIGVFTNPKRDLWISEAEPSADAVKSGAD
Aspergillus niger      MATATVLE-----------KANIGVFTNTKEDLWVADAKPTLEEVKNGQG
Aspergillus oryzae     MATATVLE-----------KANIGVYTNTNHDLWVAESKPTLEEVKSGES
Aspergillus fumigatus  MATATPTVLE---------KPNIGVYTNPKRDLWIAESTPTLEDVKSGNG
                       : .::              *.****:**.:****::::.*:..:.*:.*

Neurospora crassa      LKEGEVTVAVRSTGIGSDVRFWKHGCISPMIVECDRVLGSAGEVIAV
Hypocrea jecorina      LKPGEVTIAVRSTGIGSDVRFWHAGCIGPMIVEGDHILGSAGEVIAV
Aspergillus niger      LQPGEVTIEVRSTGIGSDVRFWHAGCIGPMIVTGDHILGSAGQVVAV
Aspergillus oryzae     LKPGEVTVQVRSTGIGSDVRFWHAGCISPMIVTGDHILGSAGEVIAV
Aspergillus fumigatus  LKPGEVTIEVRSTGIGSDVRFWHAGCIGPMIVEGDHILGSAGQVIAV
                       *:.****:.*****************.********..**:.*****.*:.*

↓ ↓ ↓        ↓

Neurospora crassa      HPSVKSIKVGDRVAIEPQVICNACEPCLTGRYNGCERVDFLSTPPVPGLL
Hypocrea jecorina      HPTVSSLQISDRVAIEPNIICNACEPCLTGRYNGCEKVEFLSTPPVPGLL
Aspergillus niger      APDVTSLKPGDRVAVEPNIICNACEPCLTGRYNCCENVQFLSTPPVDGLL
Aspergillus oryzae     ASDVTHLKPGDRVAVEPNIPCHACEPCLTGRYNGCEKVLFLSTPPVDGLL
Aspergillus fumigatus  APDVTSLKPGDRVAIEPNIPCHACEPCLTGRYNGCLNVAFLSTPPVDGLL
                       . *. :: *****:**:: *:.************.*.*******.***

Neurospora crassa      RRYVNHPAVWCRKIGNMSYENGAMLEPLSVALAGLQRAGVRLGDPVLICG
Hypocrea jecorina      RKYVNHPAVWCHKIGNMSWENGALLEPLSVALACMQPAVQLGDPVLVCG
Aspergillus niger      RRYVNHPAIWCHKIGDMSYEDGALLEPLSVSLAGIERSGLRLGDPCLVTG
Aspergillus oryzae     RRYVNHPAVWCRKIGDMSYEDGALLEPLSVSLAAIERSGLRLGDPVLVTG
Aspergillus fumigatus  RRYVNHPAVWCRKIGDMSFEDGALLEPLSVSLAAIERSGLRLGDPCLITG
                       *:********:**:***:*:*:****:****:**.:::*:.:****.*:.*

Neurospora crassa      AGPIGLITMLCAKAAGACPLVITDIDEGRLKFAKEICPEVVTHKVER-LS
Hypocrea jecorina      AGPIGLVSMLCAAAAGACPLVITDISESRLAFAKEICPRVTTHRIEIGKS
Aspergillus niger      AGPICLITLLSARAAGASPIVITDIDEGRLEFAKSLVPDVRTYKVQIGLS
Aspergillus oryzae     AGPIGLITILSARAAGATPIVITDIDEGRLAFAKSLVFDVITYKVQTNLS
Aspergillus fumigatus  AGPIGLITILSAKAAGATPLVITDIDEGRLQFAKSLVPEVRTYKVQFGLS
                       ****::::*.:*.****.*:****.:*.**.***.:.*.*.*.::::.*

Neurospora crassa      AEESAKKIVESFG--------GIEPAVALECTGVESSIAAAIWAVKFGGK
Hypocrea jecorina      AEETAKSLVSSFG--------GVEPAVTLECTGVESSIAAAIWASFPGGK
Aspergillus niger      AEQNAEGIINVFNDGQGSGPGALRPRIAMECTGVESSVASAIWSVKFGGK
Aspergillus oryzae     AEDNAAGIIDAFNDGQGSAPDALKPKLALECTGVESSVASAIWSVKFGGK
Aspergillus fumigatus  AEEQANAIINVFNDGQGSCPDALRPRLALECTGVESSVASAIWSVKFGGK
                       **: * *:. *.        . .* :::*********:*:***..*****

Neurospora crassa      VFVIGVGKNEIQIPFMRASVREVDLQFQYRYCNTWPRAIRLVENGLVDLT
Hypocrea jecorina      VFVIGVGKNEISIPFMRASVREVDIQLQYRSNTWPRAIRLIESGVIDLS
Aspergillus niger      VFVIGVGKNEMTVPFMRLSTWEIDLQYQYRYCNTWPRAIRLVRNGVIDLK
Aspergillus oryzae     VFVIGVGKNEMKIPFMRLSTQEIDLQYQYRYCNTWPRAIRLVRNGVISLK
Aspergillus fumigatus  VFVIGVGKNEMTIPFMRLSTQEIDLQYQYRYCNTWPRAIPLVQNGVINLK
                       *********:.:****.*:.*:*.*:*:.********:*.*.*::.*

Neurospora crassa      RLVTHRFPLEDALKAFETASDPKTGAIKVQIQSLE------------
Hypocrea jecorina      RFVTHRFPLEDAVKAFETSADPKSAIKVMIQSLD------------
Aspergillus niger      KLVTHRFLIEDAIKAFETAANPKTGAIKVQIMSSEDDVKAASAGQKI
Aspergillus oryzae     KLVTHRFLLEDALKAFETAADPKTGAIKVQIMSNEEDVKGASA----
Aspergillus fumigatus  RLVTHRFALEDALKAFETAANPKTGAIKVQIMSSEEDVKAASATQ--
                       ::*****..***:*****::.**:.*.*****.*.*:..:
```

FIG. 6

SEQUENCE LISTING

<160> NUMBER OF SEQ ID NOS: 9

<210> SEQ ID NO 1

<211> LENGTH: 363
<212> TYPE: PRT
<213> ORGANISM: Neurospora crassa

<400> SEQUENCE: 1

```
Met Ala Ser Ser Ala Ser Lys Thr Asn Ile Gly Val Phe Thr Asn Pro
1               5                   10                  15

Gln His Asp Leu Trp Ile Ser Glu Ala Ser Pro Ser Leu Glu Ser Val
            20                  25                  30

Gln Lys Gly Glu Glu Leu Lys Glu Gly Glu Val Thr Val Ala Val Arg
        35                  40                  45

Ser Thr Gly Ile Cys Gly Ser Asp Val His Phe Trp Lys His Gly Cys
    50                  55                  60

Ile Gly Pro Met Ile Val Glu Cys Asp His Val Leu Gly His Glu Ser
65                  70                  75                  80

Ala Gly Glu Val Ile Ala Val His Pro Ser Val Lys Ser Ile Lys Val
                85                  90                  95

Gly Asp Arg Val Ala Ile Glu Pro Gln Val Ile Cys Asn Ala Cys Glu
            100                 105                 110

Pro Cys Leu Thr Gly Arg Tyr Asn Gly Cys Glu Arg Val Asp Phe Leu
        115                 120                 125

Ser Thr Pro Pro Val Pro Gly Leu Leu Arg Arg Tyr Val Asn His Pro
    130                 135                 140

Ala Val Trp Cys His Lys Ile Gly Asn Met Ser Tyr Glu Asn Gly Ala
145                 150                 155                 160

Met Leu Glu Pro Leu Ser Val Ala Leu Ala Gly Leu Gln Arg Ala Gly
                165                 170                 175

Val Arg Leu Gly Asp Pro Val Leu Ile Cys Gly Ala Gly Pro Ile Gly
            180                 185                 190

Leu Ile Thr Met Leu Cys Ala Lys Ala Ala Gly Ala Cys Pro Leu Val
        195                 200                 205

Ile Thr Asp Ile Asp Glu Gly Arg Leu Lys Phe Ala Lys Glu Ile Cys
    210                 215                 220

Pro Glu Val Val Thr His Lys Val Glu Arg Leu Ser Ala Glu Glu Ser
225                 230                 235                 240

Ala Lys Lys Ile Val Glu Ser Phe Gly Gly Ile Glu Pro Ala Val Ala
                245                 250                 255

Leu Glu Cys Thr Gly Val Glu Ser Ser Ile Ala Ala Ile Trp Ala
            260                 265                 270

Val Lys Phe Gly Gly Lys Val Phe Val Ile Gly Val Gly Lys Asn Glu
        275                 280                 285

Ile Gln Ile Pro Phe Met Arg Ala Ser Val Arg Glu Val Asp Leu Gln
    290                 295                 300

Phe Gln Tyr Arg Tyr Cys Asn Thr Trp Pro Arg Ala Ile Arg Leu Val
305                 310                 315                 320

Glu Asn Gly Leu Val Asp Leu Thr Arg Leu Val Thr His Arg Phe Pro
                325                 330                 335

Leu Glu Asp Ala Leu Lys Ala Phe Glu Thr Ala Ser Asp Pro Lys Thr
            340                 345                 350

Gly Ala Ile Lys Val Gln Ile Gln Ser Leu Glu
        355                 360
```

<210> SEQ ID NO 2
<211> LENGTH: 1092
<212> TYPE: DNA
<213> ORGANISM: Neurospora crassa

<400> SEQUENCE: 2

```
atggcttcta gcgcttccaa gaccaacatt ggcgttttca ccaaccctca gcatgatctg      60
tggatcagcg aggcctctcc ctctctcgag agcgtccaaa agggcgaaga gctgaaggaa     120
ggcgaggtca ctgttgccgt ccgaagcaca ggcatttgcg gatccgacgt ccacttctgg     180
aagcatggtt gcatcggccc catgatcgtc gaatgcgatc atgtcctcgg ccacgagtcg     240
gcaggcgagg tcattgctgt ccatcccagc gtcaagagca tcaaggtcgg cgacagggtt     300
gccattgagc cccaagtcat ctgcaatgcc tgcgagccct gcctgactgg ccgttacaac     360
ggatgcgagc gcgttgactt cctctctacg ccccctgtgc ccggccttct ccgccgctac     420
gttaaccacc ctgccgtgtg gtgccacaaa atcggtaaca tgtcctatga aacggtgcc      480 atgctcgagc cccttcccgt ggcgctggcc ggtcttcaga gagccggtgt cgtctgggc      540 gaccctgtcc tcatctgtgg tgccggcccc attggtctga tcaccatgct ctgcgccaag     600
gccgctggtg cctgccctct tgtcattacc gacattgacg aaggccgctt gaagttcgcc     660
aaggagatct gccccgaggt cgtcacccac aaggtcgagc gcctgtcggc cgaggagtcg     720
gccaagaaga tcgtcgagag ctttggtgga atcgagcccg cggtggctct cgagtgtact     780
ggtgtcgaga gcagtatcgc ggctgctatc tgggccgtca agttcggcgg caaggtgttc     840
gtcatcggcg tgggcaagaa cgagatccag attccttca tgcgcgccag tgtgcgcgag      900
gtcgacctgc agttccagta ccgttactgc aacacttggc ccagggccat cgcctggtc      960 gagaatggcc tcgttgacct caccaggctg gtgacgcacc gtttcccgtt ggaggatgcg    1020
ctcaaggcgt tcgagacggc gtcagacccc aagacgggtg ccatcaaggt gcagatccag    1080
agtctggagt aa                                                         1092
```

<210> SEQ ID NO 3
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 3

```
gtagctacgt cagaattcca tggcttctag cgcttcc                               37
```

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 4

```
gctgattctg cggccgctta ctccagactc tggatc                                36
```

<210> SEQ ID NO 5
<211> LENGTH: 376
<212> TYPE: PRT
<213> ORGANISM: Hypocrea jecorina

<400> SEQUENCE: 5

```
Met Ser Pro Ser Ala Val Asp Asp Ala Pro Lys Ala Thr Gly Ala Ala
1               5                   10                  15

Ile Ser Val Lys Pro Asn Ile Gly Val Phe Thr Asn Pro Lys His Asp
            20                  25                  30
```

Leu Trp Ile Ser Glu Ala Glu Pro Ser Ala Asp Ala Val Lys Ser Gly
             35                  40                  45

Ala Asp Leu Lys Pro Gly Val Thr Ile Ala Val Arg Ser Thr Gly
 50                  55                  60

Ile Cys Gly Ser Asp Val His Phe Trp His Ala Gly Cys Ile Gly Pro
 65                  70                  75                  80

Met Ile Val Glu Gly Asp His Ile Leu Gly His Glu Ser Ala Gly Glu
                 85                  90                  95

Val Ile Ala Val His Pro Thr Val Ser Ser Leu Gln Ile Gly Asp Arg
            100                 105                 110

Val Ala Ile Glu Pro Asn Ile Ile Cys Asn Ala Cys Glu Pro Cys Leu
            115                 120                 125

Thr Gly Arg Tyr Asn Gly Cys Glu Lys Val Glu Phe Leu Ser Thr Pro
        130                 135                 140

Pro Val Pro Gly Leu Leu Arg Arg Tyr Val Asn His Pro Ala Val Trp
145                 150                 155                 160

Cys His Lys Ile Gly Asn Met Ser Trp Glu Asn Gly Ala Leu Leu Glu
                165                 170                 175

Pro Leu Ser Val Ala Leu Ala Gly Met Gln Arg Ala Lys Val Gln Leu
            180                 185                 190

Gly Asp Pro Val Leu Val Cys Ala Gly Pro Ile Gly Leu Val Ser Met
        195                 200                 205

Leu Cys Ala Ala Ala Ala Gly Ala Cys Pro Leu Val Ile Thr Asp Ile
210                 215                 220

Ser Glu Ser Arg Leu Ala Phe Ala Lys Glu Ile Cys Pro Arg Val Thr
225                 230                 235                 240

Thr His Arg Ile Glu Ile Gly Lys Ser Ala Glu Thr Ala Lys Ser
                245                 250                 255

Ile Val Ser Ser Phe Gly Gly Val Glu Pro Ala Val Thr Leu Glu Cys
            260                 265                 270

Thr Gly Val Glu Ser Ser Ile Ala Ala Ala Ile Trp Ala Ser Lys Phe
        275                 280                 285

Gly Gly Lys Val Phe Val Ile Gly Val Gly Lys Asn Glu Ile Ser Ile
290                 295                 300

Pro Phe Met Arg Ala Ser Val Arg Glu Val Asp Ile Gln Leu Gln Tyr
305                 310                 315                 320

Arg Tyr Ser Asn Thr Trp Pro Arg Ala Ile Arg Leu Ile Glu Ser Gly
                325                 330                 335

Val Ile Asp Leu Ser Lys Phe Val Thr His Arg Phe Pro Leu Glu Asp
            340                 345                 350

Ala Val Lys Ala Phe Glu Thr Ser Ala Asp Pro Lys Ser Gly Ala Ile
        355                 360                 365

Lys Val Met Ile Gln Ser Leu Asp
    370                 375

<210> SEQ ID NO 6
<211> LENGTH: 386
<212> TYPE: PRT
<213> ORGANISM: Aspergillus niger

<400> SEQUENCE: 6

Met Ala Thr Ala Thr Val Leu Glu Lys Ala Asn Ile Gly Val Phe Thr
  1               5                  10                  15

Asn Thr Lys His Asp Leu Trp Val Ala Asp Ala Lys Pro Thr Leu Glu
             20                  25                  30

```
Glu Val Lys Asn Gly Gln Gly Leu Gln Pro Gly Glu Val Thr Ile Glu
             35                  40                  45

Val Arg Ser Thr Gly Ile Cys Gly Ser Asp Val His Phe Trp His Ala
 50                  55                  60

Gly Cys Ile Gly Pro Met Ile Val Thr Gly Asp His Ile Leu Gly His
 65                  70                  75                  80

Glu Ser Ala Gly Gln Val Val Ala Val Ala Pro Asp Val Thr Ser Leu
                 85                  90                  95

Lys Pro Gly Asp Arg Val Ala Val Glu Pro Asn Ile Ile Cys Asn Ala
                100                 105                 110

Cys Glu Pro Cys Leu Thr Gly Arg Tyr Asn Gly Cys Glu Asn Val Gln
            115                 120                 125

Phe Leu Ser Thr Pro Pro Val Asp Gly Leu Leu Arg Arg Tyr Val Asn
        130                 135                 140

His Pro Ala Ile Trp Cys His Lys Ile Gly Asp Met Ser Tyr Glu Asp
145                 150                 155                 160

Gly Ala Leu Leu Glu Pro Leu Ser Val Ser Leu Ala Gly Ile Glu Arg
                    165                 170                 175

Ser Gly Leu Arg Leu Gly Asp Pro Cys Leu Val Thr Gly Ala Gly Pro
                180                 185                 190

Ile Gly Leu Ile Thr Leu Leu Ser Ala Arg Ala Ala Gly Ala Ser Pro
            195                 200                 205

Ile Val Ile Thr Asp Ile Asp Glu Gly Arg Leu Glu Phe Ala Lys Ser
        210                 215                 220

Leu Val Pro Asp Val Arg Thr Tyr Lys Val Gln Ile Gly Leu Ser Ala
225                 230                 235                 240

Glu Gln Asn Ala Glu Gly Ile Ile Asn Val Phe Asn Asp Gly Gln Gly
                    245                 250                 255

Ser Gly Pro Gly Ala Leu Arg Pro Arg Ile Ala Met Glu Cys Thr Gly
                260                 265                 270

Val Glu Ser Ser Val Ala Ser Ala Ile Trp Ser Val Lys Phe Gly Gly
            275                 280                 285

Lys Val Phe Val Ile Gly Val Gly Lys Asn Glu Met Thr Val Pro Phe
        290                 295                 300

Met Arg Leu Ser Thr Trp Glu Ile Asp Leu Gln Tyr Gln Tyr Arg Tyr
305                 310                 315                 320

Cys Asn Thr Trp Pro Arg Ala Ile Arg Leu Val Arg Asn Gly Val Ile
                    325                 330                 335

Asp Leu Lys Lys Leu Val Thr His Arg Phe Leu Leu Glu Asp Ala Ile
                340                 345                 350

Lys Ala Phe Glu Thr Ala Ala Asn Pro Lys Thr Gly Ala Ile Lys Val
            355                 360                 365

Gln Ile Met Ser Ser Glu Asp Asp Val Lys Ala Ser Ala Gly Gln
        370                 375                 380

Lys Ile
385

<210> SEQ ID NO 7
<211> LENGTH: 382
<212> TYPE: PRT
<213> ORGANISM: Aspergillus oryzae

<400> SEQUENCE: 7

Met Ala Thr Ala Thr Val Leu Glu Lys Ala Asn Ile Gly Val Tyr Thr
 1               5                  10                  15
```

Asn Thr Asn His Asp Leu Trp Val Ala Glu Ser Lys Pro Thr Leu Glu
            20                  25                  30

Glu Val Lys Ser Gly Glu Ser Leu Lys Pro Gly Glu Val Thr Val Gln
        35                  40                  45

Val Arg Ser Thr Gly Ile Cys Gly Ser Asp Val His Phe Trp His Ala
 50                  55                  60

Gly Cys Ile Gly Pro Met Ile Val Thr Gly Asp His Ile Leu Gly His
65                  70                  75                  80

Glu Ser Ala Gly Glu Val Ile Ala Val Ala Ser Asp Val Thr His Leu
                85                  90                  95

Lys Pro Gly Asp Arg Val Ala Val Glu Pro Asn Ile Pro Cys His Ala
            100                 105                 110

Cys Glu Pro Cys Leu Thr Gly Arg Tyr Asn Gly Cys Glu Lys Val Leu
        115                 120                 125

Phe Leu Ser Thr Pro Pro Val Asp Gly Leu Leu Arg Arg Tyr Val Asn
130                 135                 140

His Pro Ala Val Trp Cys His Lys Ile Gly Asp Met Ser Tyr Glu Asp
145                 150                 155                 160

Gly Ala Leu Leu Glu Pro Leu Ser Val Ser Leu Ala Ala Ile Glu Arg
                165                 170                 175

Ser Gly Leu Arg Leu Gly Asp Pro Val Leu Val Thr Gly Ala Gly Pro
            180                 185                 190

Ile Gly Leu Ile Thr Leu Leu Ser Ala Arg Ala Ala Gly Ala Thr Pro
        195                 200                 205

Ile Val Ile Thr Asp Ile Asp Glu Gly Arg Leu Ala Phe Ala Lys Ser
210                 215                 220

Leu Val Pro Asp Val Ile Thr Tyr Lys Val Gln Thr Asn Leu Ser Ala
225                 230                 235                 240

Glu Asp Asn Ala Ala Gly Ile Ile Asp Ala Phe Asn Asp Gly Gln Gly
                245                 250                 255

Ser Ala Pro Asp Ala Leu Lys Pro Lys Leu Ala Leu Glu Cys Thr Gly
            260                 265                 270

Val Glu Ser Ser Val Ala Ser Ala Ile Trp Ser Val Lys Phe Gly Gly
        275                 280                 285

Lys Val Phe Val Ile Gly Val Gly Lys Asn Glu Met Lys Ile Pro Phe
290                 295                 300

Met Arg Leu Ser Thr Gln Glu Ile Asp Leu Gln Tyr Gln Tyr Arg Tyr
305                 310                 315                 320

Cys Asn Thr Trp Pro Arg Ala Ile Arg Leu Val Arg Asn Gly Val Ile
                325                 330                 335

Ser Leu Lys Lys Leu Val Thr His Arg Phe Leu Leu Glu Asp Ala Leu
            340                 345                 350

Lys Ala Phe Glu Thr Ala Ala Asp Pro Lys Thr Gly Ala Ile Lys Val
        355                 360                 365

Gln Ile Met Ser Asn Glu Glu Asp Val Lys Gly Ala Ser Ala
370                 375                 380

<210> SEQ ID NO 8
<211> LENGTH: 386
<212> TYPE: PRT
<213> ORGANISM: Aspergillus fumigatus

<400> SEQUENCE: 8

Met Ala Thr Ala Thr Thr Thr Val Leu Glu Lys Pro Asn Ile Gly Val
1               5                   10                  15

Tyr Thr Asn Pro Lys His Asp Leu Trp Ile Ala Glu Ser Thr Pro Thr
            20                  25                  30
Leu Glu Asp Val Lys Ser Gly Asn Gly Leu Lys Pro Gly Glu Val Thr
        35                  40                  45
Ile Glu Val Arg Ser Thr Gly Ile Cys Gly Ser Asp Val His Phe Trp
50                  55                  60
His Ala Gly Cys Ile Gly Pro Met Ile Val Glu Gly Asp His Ile Leu
65                  70                  75                  80
Gly His Glu Ser Ala Gly Gln Val Ile Ala Val Ala Pro Asp Val Thr
                85                  90                  95
Ser Leu Lys Pro Gly Asp Arg Val Ala Ile Glu Pro Asn Ile Pro Cys
            100                 105                 110
His Ala Cys Glu Pro Cys Leu Thr Gly Arg Tyr Asn Gly Cys Leu Asn
        115                 120                 125
Val Ala Phe Leu Ser Thr Pro Pro Val Asp Gly Leu Leu Arg Arg Tyr
130                 135                 140
Val Asn His Pro Ala Val Trp Cys His Lys Ile Gly Asp Met Ser Phe
145                 150                 155                 160
Glu Asp Gly Ala Leu Leu Glu Pro Leu Ser Val Ser Leu Ala Ala Ile
                165                 170                 175
Glu Arg Ser Gly Leu Arg Leu Gly Asp Pro Cys Leu Ile Thr Gly Ala
            180                 185                 190
Gly Pro Ile Gly Leu Ile Thr Leu Leu Ser Ala Lys Ala Ala Gly Ala
        195                 200                 205
Thr Pro Leu Val Ile Thr Asp Ile Asp Glu Gly Arg Leu Gln Phe Ala
210                 215                 220
Lys Ser Leu Val Pro Glu Val Arg Thr Tyr Lys Val Gln Phe Gly Leu
225                 230                 235                 240
Ser Ala Glu Glu Gln Ala Asn Ala Ile Ile Asn Val Phe Asn Asp Gly
                245                 250                 255
Gln Gly Ser Gly Pro Asp Ala Leu Arg Pro Arg Leu Ala Leu Glu Cys
            260                 265                 270
Thr Gly Val Glu Ser Ser Val Ala Ser Ala Ile Trp Ser Val Lys Phe
        275                 280                 285
Gly Gly Lys Val Phe Val Ile Gly Val Gly Lys Asn Glu Met Thr Ile
290                 295                 300
Pro Phe Met Arg Leu Ser Thr Gln Glu Ile Asp Leu Gln Tyr Gln Tyr
305                 310                 315                 320
Arg Tyr Cys Asn Thr Trp Pro Arg Ala Ile Arg Leu Val Gln Asn Gly
                325                 330                 335
Val Ile Asn Leu Lys Arg Leu Val Thr His Arg Phe Ala Leu Glu Asp
            340                 345                 350
Ala Leu Lys Ala Phe Glu Thr Ala Ala Asn Pro Lys Thr Gly Ala Ile
        355                 360                 365
Lys Val Gln Ile Met Ser Ser Glu Glu Asp Val Lys Ala Ala Ser Ala
370                 375                 380
Thr Gln
385

<210> SEQ ID NO 9
<211> LENGTH: 5
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 9

Gly Ser Pro Asn Ser
1               5
```

ARABINITOL DEHYDROGENASE FROM *NEUROSPORA CRASSA*

This application is a Divisional of co-pending U.S. patent application Ser. No. 12/235,253, filed Sep. 22, 2008, which claims priority to U.S. Provisional Application No. 60/975,023, filed Sep. 25, 2007, the contents of which applications are herein incorporated by reference in their entireties.

BACKGROUND

L-arabinitol 4-dehydrogenases (LAD) from *Neurospora crassa* and their uses in production of sugar alcohols including xylitol from arabinose containing media are disclosed.

Lignocellulosic biomass represents a renewable resource that is available in sufficient quantities from the corn wet-milling industry to serve as a low-cost feedstock. Some sources, particularly corn fiber, contain significant amounts of L-arabinose, an abundant pentose sugar second only to D-xylose in biomass composition. However, utilization of the L-arabinose content from hemicellulose hydrolysates for production of valued products has resulted in limited success. The inability of many yeasts and fungi to ferment L-arabinose appears to be a consequence of inefficient or incomplete assimilation pathways for this pentose sugar. It has also been suggested that the cofactor imbalance necessary for the catabolism of L-arabinose also plays a factor. Recently some progress has been made with the overexpression of either the bacterial utilization pathway or the fungal pathway for production of ethanol from L-arabinose. One benefit of utilizing the fungal pathway is that the intermediate xylitol is also formed, which is a five-carbon sugar alcohol that has attracted much attention because of its potential as a natural food sweetener, a dental caries reducer, and a sugar substitute for diabetics.

Xylitol is a pentitol and is used not only as a sweetener but also as a platform chemical for the production of industrially important chemicals. Studies have shown that among sugar substitutes, xylitol is one of the most promising candidates for application in a wide range of products due to several favorable properties. These include anti-cariogenicity, suitability for use by diabetic patients, and good gastrointestinal tolerance, in addition to possibly preventing osteoporosis and ear infections. In spite of its advantages, the use of xylitol is currently limited and falls well short of another, cheaper sugar alternative, sorbitol in the billion dollar polyol market. Other than its use as a sweetener, xylitol is also an industrially important chemical, and the US Department of Energy (DOE) has named it among one of their top 12 platform chemicals from agricultural sources.

L-arabinitol 4-dehydrogenase (LAD, EC 1.1.1.12), a common enzyme found in yeasts and filamentous fungi, catalyzes the second step of the recently elucidated fungal L-arabinose metabolic pathway by oxidizing L-arabinitol to L-xylulose with concomitant NAD+ reduction. LAD is purportedly a fungal orthologue of the eukaryotic sorbitol dehydrogenase (SDH) and belongs to the family of zinc-containing alcohol dehydrogenases. Several LADs have successfully been cloned and expressed. However, they are not optimal for in vitro enzymatic production of xylitol due to their poor stability and/or activity.

L-arabinose is a major constituent of some plant materials, up to 15% of materials such as wheat bran and corn cob hulls, so that L-arabinose processing is of relevance for microorganisms using plant material as a carbon source. The bacterial pathway for L-arabinose catabolism is known. It includes an isomerase, a kinase, and an epimerase that sequentially convert L-arabinose to L-ribulose, L-ribulose 5-phosphate, and D-xylulose 5-phosphate. D-xylulose 5-phosphate is an intermediate of the pentose phosphate pathway. There is also a pathway for fungi that may include five enzymes, aldose reductase, L-arabinitol 4-dehydrogenase, L-xylulose reductase, xylitol dehydrogenase, and xylulokinase. The intermediates are, in this order: L-arabinitol, L-xylulose, xylitol and D-xylulose.

SUMMARY

Cloning, heterologous expression, purification, and characterization of a new L-arabinitol 4-dehydrogenase (LAD) from *Neurospora crassa* are disclosed herein. This enzyme is very stable and active compared to other known arabinitol dehydrogenases.

An NAD+-dependent L-arabinitol 4-dehydrogenase (LAD, EC 1.1.1.12) from *Neurospora crassa* was cloned and recombinantly expressed in *Escherichia coli* and purified to homogeneity. The enzyme was a homotetramer with a subunit molecular mass of 39,245 Da, and contains two $Zn^{2+}$ ions per subunit, displaying similar characteristics to medium-chain sorbitol dehydrogenases. $K_m$ values for substrates L-arabinitol, adonitol, and xylitol were 16 mM, 35 mM, and 290 mM, respectively. The enzyme showed strong preference for $NAD^+$, with a $K_m$ of 174 µM, but also displayed very low yet detectable activity with $NADP^+$. No activity was observed for D-mannitol, D-arabinitol, or D-sorbitol. The optimum activity was between 45-55° C. The pH optimum was approximately pH 9.5, and >60% of the activity remained in the pH span from 8.0 to 10.5. This enzyme is one of the most stable and active LADs ever reported, and is useful for in vivo and in vitro production of xylitol and ethanol from L-arabinose.

A purified arabinitol dehydrogenase includes an amino acid sequence of SEQ ID NO: 1. An arabinitol dehydrogenase may be recombinant and may be heterologously expressed. In an aspect, purified arabinitol dehydrogenase includes a fusion protein. The purity of purified arabinitol dehydrogenases disclosed herein may range from about 85% to 90% and from about 90% to about 95% or 99%.

Arabinitol dehydrogenases disclosed herein include an amino acid sequence that is equal to or greater than or at least about 85% or 90% or 95% or 99% similar to SEQ ID NO: 1, which include spontaneous mutations or random variations. Arabinitol dehydrogenases disclosed herein include a nucleic acid sequence that is equal to or greater than or at least about 80% or 85% or 90% or 95% or 99% similar to SEQ ID NO: 2, which include spontaneous mutations or random variations.

A suitable heterologous host for expressing and purifying arabinitol dehydrogenases disclosed herein include for example, bacteria, yeast, and plants.

An isolated nucleic acid sequence encoding an arabinitol dehydrogenase includes a nucleic acid sequence designated by SEQ ID NO: 2. The nucleic acid of arabinitol dehydrogenase may be directly isolated from *Neurospora crassa* or may also be directly synthesized or may also be recombinantly generated.

Arabinitol dehydrogenases disclosed herein are useful in producing xylitol, ethanol and any suitable sugar alcohol. For example, an arabinitol dehydrogenase is useful in producing ethanol from a plant material, such as corn. Production of ethanol may be by fermentation.

In an aspect, the production of xylitol or ethanol utilizes a phosphite dehydrogenase-based NADP regeneration system. Purified arabinitol dehydrogenases are useful to metabolically enhance an organism used for fermentation of a plant biomass to produce ethanol.

A method of producing ethanol includes:
(a) obtaining a purified arabinitol dehydrogenase that includes an amino acid sequence of SEQ ID NO: 1; and
(b) providing conditions to produce ethanol from an arabinose containing medium.

A method of producing xylitol includes:
(a) obtaining a purified arabinitol dehydrogenase that includes an amino acid sequence of SEQ ID NO: 1; and
(b) providing conditions to produce xylitol from an arabinose containing medium.

A heterologous host expressing an arabinitol dehydrogenase includes for example, *Escherichia coli*, *Saccharomyces cerevisiae*, and a plant cell.

BRIEF DESCRIPTION OF THE DRAWINGS

FIG. 6 shows amino acid sequence alignment of *N. crassa* LAD (SEQ ID NO: 1) with four other closely related LAD sequences (SEQ ID NOS 5-8, respectively, in order of appearance) from filamentous fungi and yeast. Residues highlighted in gray represent the four conserved residues that make up the catalytic zinc binding tetrad. Residues indicated by arrows represent the four conserved cysteine residues that make up the proposed structural zinc binding tetrad.

DETAILED DESCRIPTION

Figure 1:
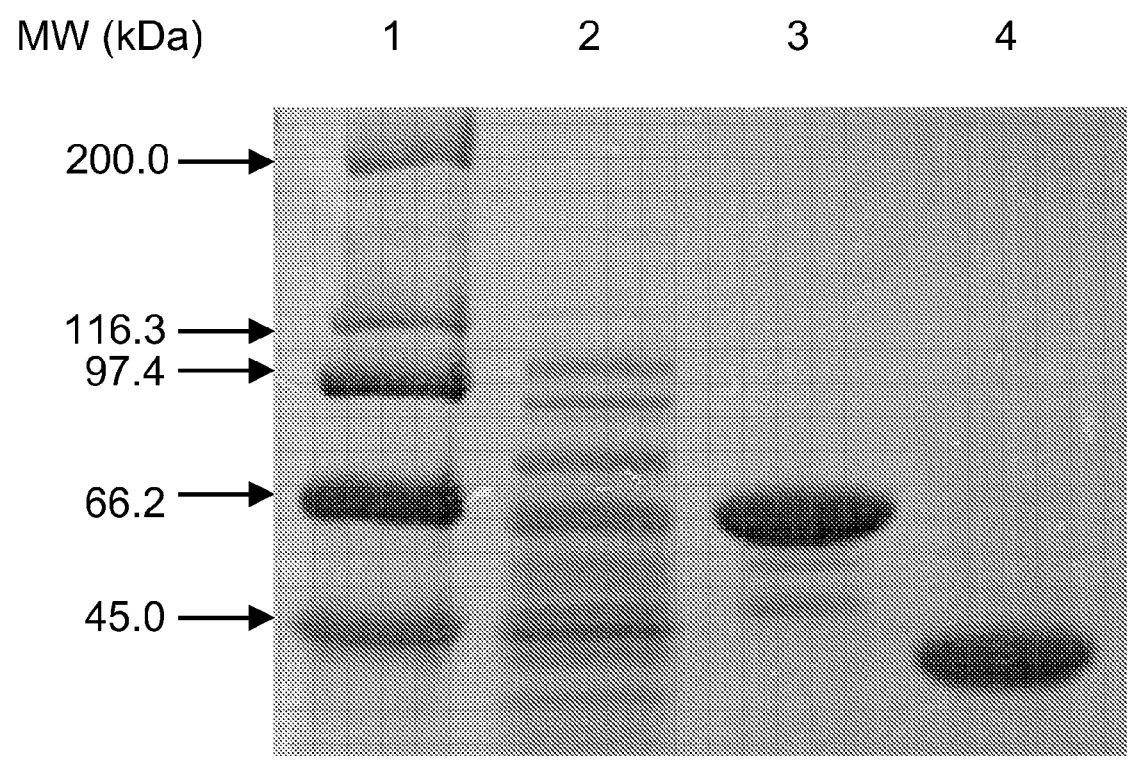
FIG. 1 shows overexpression and purification of recombinant *N. crassa* LAD. Lane 1, the molecular weight marker proteins (size in kDa is shown); lane 2, cell-free crude extract; lane 3, purified LAD enzyme with N-terminal GST-tag; lane 4, purified LAD enzyme with GST-tag removed by thrombin cleavage.

NCU00643.1 (EAA36547.1) (hypothetical) from *N. crassa* was found to encode an L-arabinitol 4-dehydrogenase of 363 amino acid residues with a calculated MW of 39,245. Sequence alignment with other reported LADs shows sequence similarity of about 70-80%, with conserved regions for $Zn^{2+}$ binding, cofactor binding, and active site residues (FIG. 6). Comparison with several mammalian SDHs (mouse, rat, bovine, sheep, and human) showed ~40% similarity, whereas comparison with xylitol dehydrogenases (*Hypocrea jecorina*, *Aspergillus oryzae*, *Candida tropicalis*, *Pichia stipitis*, and *Aspergillus fumigatus* Af293) showed ~30% similarity.

Kinetic parameters of characterized LADs from *Hypocrea jecorina*, *Aspergillus niger*, and *Aspergillus oryzae* are displayed in Table 3. The $K_m$ value of *N. crassa* LAD was 16 mM for L-arabinitol, which when compared to LADs from *H. jecorina* and *A. niger*, is one of the lower values reported of characterized LADs. With a specific activity of the purified *N. crassa* LAD equal to about 31 U/mg, it is almost 20-fold greater than *H. jecorina* LAD purified from *S. cerevisiae* heterologous expression, and orders of magnitude higher than other LADs except for *A. niger* LAD, which shows about 3-fold greater specific activity than that of *N. crassa* LAD. However, it was also reported that the purified *A. niger* LAD was highly unstable, with rapidly diminishing activity at 4° C., and complete loss of activity after freeze-thawing of the enzyme. In contrast, *N. crassa* LAD is quite stable and does not markedly lose activity when frozen repeatedly.

There has been no in-depth study of the substrate binding residues for LAD, but the enzyme has been postulated to be a fungal orthologue of the eukaryotic D-sorbitol dehydrogenases which have been investigated more thoroughly. Based on these reports, the active site substrate binding residues are all strictly conserved in all LADs characterized to date (FIG. 6). When comparing these residues in *N. crassa* LAD to sorbitol dehydrogenases, F59 was not conserved, which instead was a tyrosine residue in all of the SDHs examined. Mutational studies of this position were examined for F59A, F59S, and F59Y, to determine what effects this residue has on substrate specificity alteration, and are shown in Table 4. Replacement of the native F59 residue with the homologous tyrosine found in SDH decreased the catalytic efficiency towards all active substrates. The ability of LAD to bind each substrate markedly decreased as the size of the amino acid at position 59 was decreased. Although these results suggest this residue is important for binding and catalysis for the active substrates of the wild type LAD, it did not confer the ability to accept D-sorbitol as a substrate. Amino acids flanking the active site cleft may be responsible for the activity and affinity patterns between LAD and SDH.

A gene from *N. crassa* encoding an LAD was cloned and purified. The enzyme is highly active and stable, acts on several five carbon sugar alcohol substrates, and operates over a wide pH range. This enzyme is useful in the production of xylitol and ethanol from L-arabinose derived from renewable resources.

In certain embodiments, purified LADs are about 95% similar to SEQ ID NO: 1 and may include naturally occurring variations in *N. crassa* arabinitol dehydrogenases. In certain embodiments, arabinitol dehydrogenases disclosed herein are recombinant and/or expressed or purified from a heterologous host. Suitable heterologous hosts include for example, bacteria, yeast, and plants or plant cells. Cultures of bacteria, yeast, and plant cells in a batch reactor or a continuous flow reactor are also suitable for large-scale arabinitol dehydrogenases production.

In certain embodiments, purified arabinitol dehydrogenases disclosed herein are about 90% pure, or 95% pure or about 98% pure and generally more than about 90% pure.

Arabinitol dehydrogenases disclosed herein are capable being expressed in a variety of heterologous hosts such as bacteria, fungi, and plants. Such hosts include for example, *Escherichia coli, Saccharomyces cerevisiae*, and a plant cell. In certain embodiments, the heterologous hosts are engineered for increased arabinose uptake. The substrate or the source material need not be extensively or substantially purified and can include mixtures of sugars as found in plant biomass material.

The term "consisting essentially of" refers to a conserved portion of arabinitol dehydrogenases that include one or more amino acid positions disclosed herein that are important for the catalysis. For example, FIG. 6 shows a multiple sequence alignment showing conserved residues from a variety of arabinitol dehydrogenases, thus providing a structure-function relationship. Thus, the term consisting essentially of refers to that portion of the arabinitol dehydrogenases that are able to act catalytically and maintain similar efficiency.

Intermediates in the fungal pentose pathway, such as xylitol are also produced. For example, microbes are engineered to produce bulk amounts of xylitol, wherein the engineered microbes express at least one reductase and/or dehydrogenase during the synthesis of xylitol, in addition to the LADs disclosed herein. In certain embodiments, microbes are engineered to express xylose reductases (also referred to herein as XRs) and xylitol dehydrogenase (also referred to herein XDH) enzymes to produce xylitol from xylose (or xylulose) in vivo. For example, *E. coli* are constructed to express XDH and/or XR to produce xylitol from a substrate that includes xylose (or xylulose). Certain embodiments also provide engineered microbes capable of deriving reducing equivalents from carbon substrates (such as glucose) for the subsequent reduction of xylose or xylulose to xylitol. The contents and disclosures of co-pending PCT/US2008/069657 are herein incorporated by reference in its entirety as it relates to various xylose reductase mutants and uses thereof.

As used herein, the terms gene and polynucleotide sequence are used interchangeably. Nucleotide sequences that encode for or correspond to a particular sequence of nucleic acids (such as ribonucleic acids) or amino acids that include all or part of one or more products (such as polypeptides, proteins, or enzymes), and may or may not include regulatory sequences, such as promoter sequences, which determine, for example, the conditions under which the gene is expressed.

Many small variations in the nucleotide sequence of a gene do not significantly change the catalytic properties of the encoded arabinitol dehydrogenases disclosed herein. For example, many changes in nucleotide sequence do not change the amino acid sequence of the arabinitol dehydrogenases disclosed herein. Also an amino acid sequence can have variations which do not change the functional properties of arabinitol dehydrogenases disclosed herein, in particular they do not prevent arabinitol dehydrogenases from carrying out its catalytic function. Such variations in the nucleotide sequence of DNA molecules or in an amino acid sequence are known as "functionally equivalent variants", because they do not significantly change the function of the gene to encode a protein with a particular function, e.g. catalysing a particular reaction or, respectively, of the protein with a particular function. Thus such functionally equivalent variants, including fragments, of the nucleotide sequence of SEQ ID NO: 2 and, respectively, of the amino acid sequence of SEQ ID NO: 1, are encompassed within the scope of the disclosure.

Genetically engineered DNA molecules, e.g., a recombinant DNA, a vector, e.g., an expression vector, that includes the nucleic acid encoding the arabinitol dehydrogenases disclosed herein or their catalytically active fragments thereof are expressed in host cells, i.e. microorganisms. Arabinitol dehydrogenases disclosed herein may be operably linked to a promoter. The vector can be e.g. a conventional vector, such as a virus, e.g. a bacteriophage, or a plasmid, preferably a plasmid. The construction of an expression vector is within the skills of an artisan.

The following examples are for illustrative purposes only and are not intended to limit the scope of the disclosure.

Example 1

N. crassa LAD Gene Identification

LADs from *Hypocrea jecorina* (GenBank accession number AF355628.1) and *Aspergillus oryzae* (AB116938.2) were used as templates for a protein BLAST search. Utilizing the whole-genome sequence of *N. crassa*, a postulated hypothetical protein NCU00643.1 (EAA36547.1) was discovered that had the greatest sequence identity (~80%). This protein was later designated as *N. crassa* LAD and had significant homology (72 to 80% identity) with other LADs. Among the conserved residues were those that formed the active site and the structural $Zn^{2+}$-binding site and the glycine fingerprint found in polyol dehydrogenases, as well as the majority of those shown to bind substrate in the SDH homologues.

This example demonstrates that a hypoethetical sequence was specifically selected from a myriad of sequences and subsequently demonstrated to have the functional properties of an arabinitol dehydrogenase.

Example 2

N. crassa LAD Cloning and Expression

Figure 5:
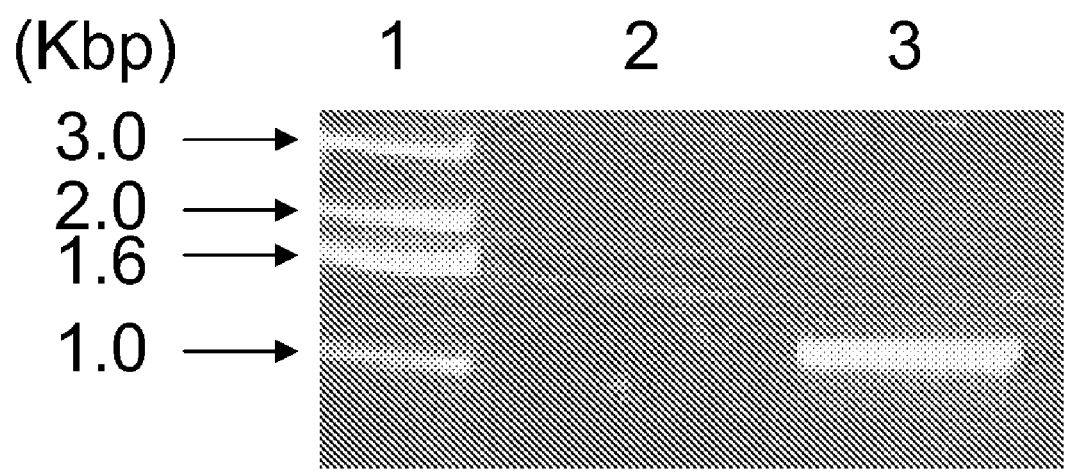
FIG. 5 shows an RT-PCR product of the *N. crassa* LAD gene. Lane 1 shows the DNA base pair ladder. Lane 2 is the control in which there was no reverse transcription. Lane 3 is the RT-PCR product amplified from *N. crassa* total RNA. The approximately 1.1 kb product in Lane 3 was the expected size for the 1080 bp *N. crassa* LAD encoding gene plus the extra primer length for cloning. This product was subsequently sequenced and determined to be the desired gene.
Figure 7A:
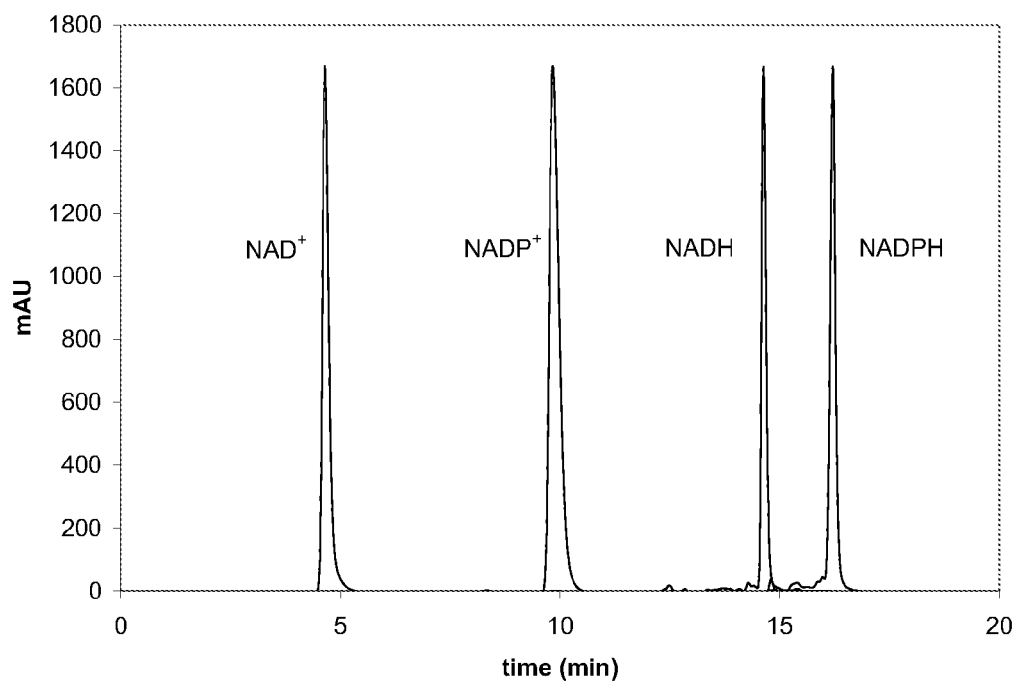
FIG. 7 shows HPLC analysis of the reaction products of *N. crassa* LAD. A) Cofactor stocks, 260 nm; B) Cofactor stocks, 340 nm; C) NAD+ reaction mix products, 340 nm; D) NADP+ reaction mix before (gray) and after (black) LAD enzyme addition, 340 nm (magnified).
Figure 7B:
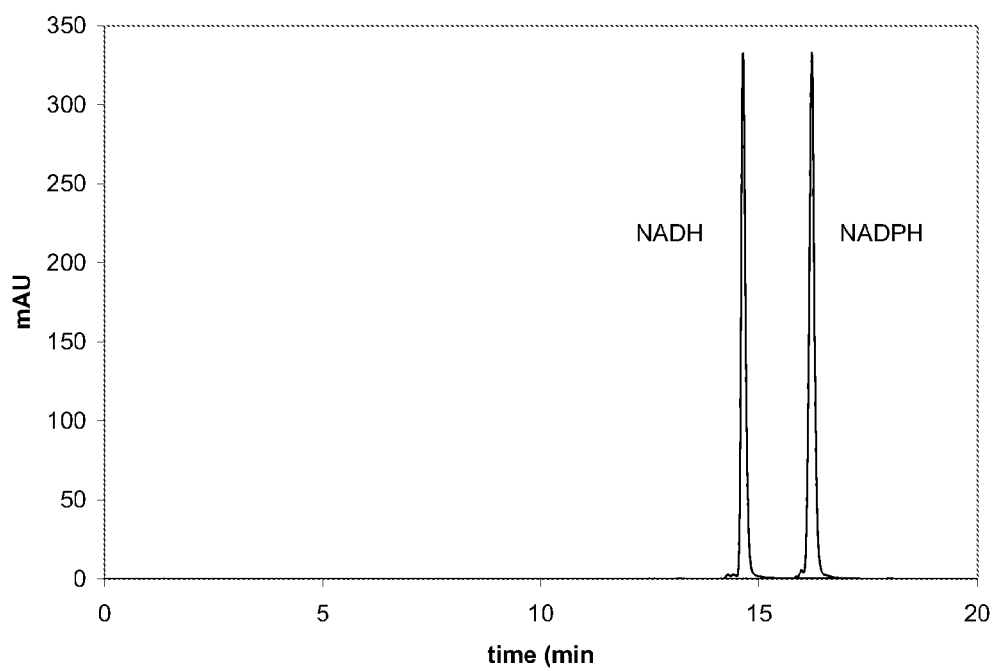
Figure 7C:
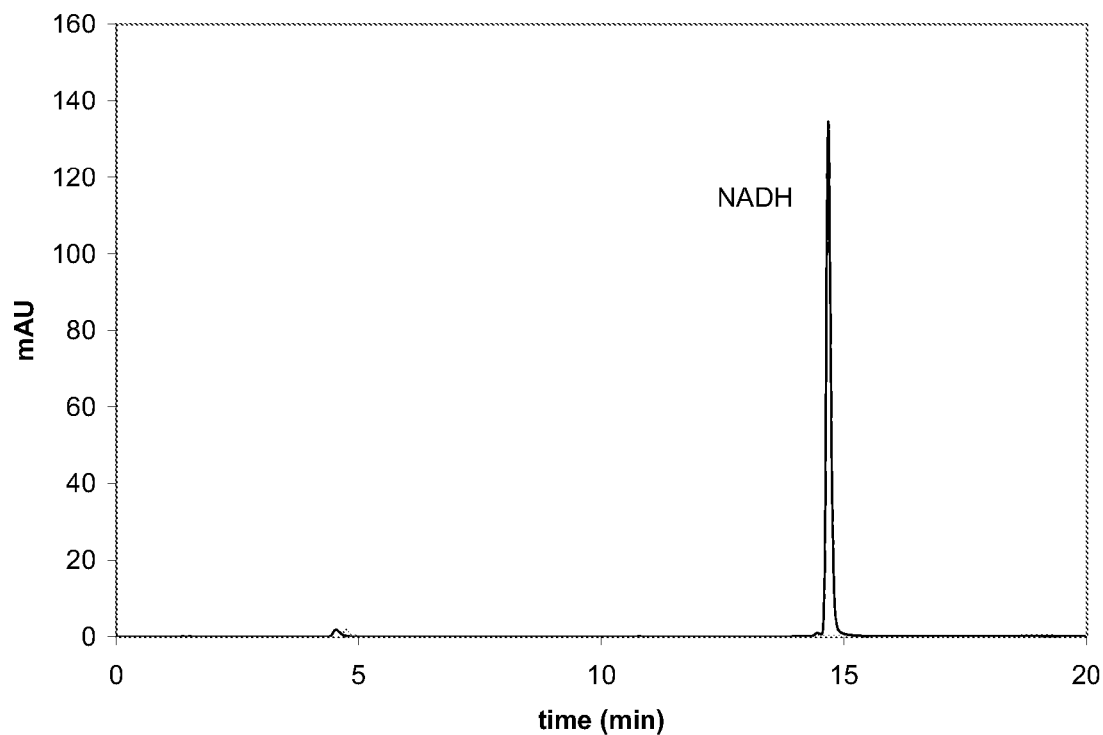
Figure 7D:
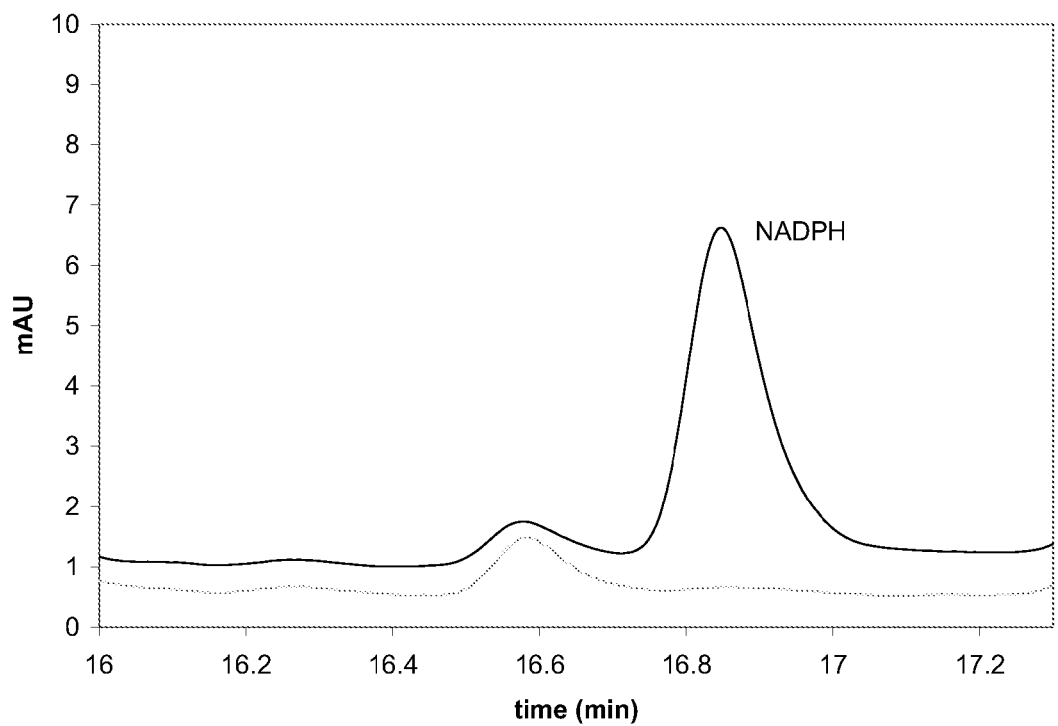

*N. crassa* RNA purification, reverse-transcription PCR, cloning, and *N. crassa* LAD expression are described in this example. Reverse transcription-PCR (RT-PCR) performed on total RNA isolated from L-arabinose-induced *N. crassa* 10333 showed the expected size of a gene product (FIG. 5). The reverse transcription-PCR product was subcloned into pGEX-4T-3 vector (Amersham Biosciences) using EcoRI and NotI restriction sites and was transformed into *Escherichia coli* BL21(DE3). This construct (pGEX-lad1) encoded *N. crassa* LAD as an N-terminal glutathione S-transferase (GST)-tagged fusion with a thrombin cleavage site. Cell lysates of isopropyl-β-D-thiogalactopyranoside (IPTG) induced cultures of these cells were prepared, analyzed by SDS-PAGE, and assayed for LAD activities. The construct produced soluble GST-tagged *N. crassa* LAD at ~16% of the total soluble cellular proteins (FIG. 1), which was then purified in a single step with a GST-Bind kit (Novagen) according to manufacturer's protocol. The purified protein was desalted by ultrafiltration with several washes of 50 mM morpholinepropanesulfonic acid (MOPS) buffer (pH 7.25). After digesting with biotinylated thrombin (Novagen), the enzyme was incubated with streptavidin agarose to remove the thrombin, and then passed through GST-Bind resin again to remove the cleaved GST-tag. GST-tagged LAD cleaved with thrombin was used for characterization purposes, as it had about 65%-greater specific activity than the tagged LAD enzyme. LAD stocks were stored frozen with 10% (v/v) glycerol at −80° C. Protein concentrations were determined by the Bradford method and by using an estimated extinction coefficient (San Diego Supercomputer Center Biology Workbench) of 35.3 mM-1 cm-1 at 280 nm with similar results. The purity of the protein was analyzed by an SDS-PAGE gel stained with Coomassie brilliant blue (FIG. 1). The final yield of protein was 30 mg/liter of culture (~9 mg/g of *E. coli*) of >95% pure LAD with a molecular mass of ~39 kDa, consistent with the predicted value of 39.6 kDa.

Example 3

Steady-State Kinetics

Initial rates were determined using a Varian Cary 100 Bio UV-visible spectrophotometer (Varian) at 25° C. in 50 mM Tris (pH 8.0). Purified *N. crassa* LAD displayed activity with NAD+ as the preferred cofactor (Table 1), although there was small yet detectable activity with NADP+, which was verified by high performance liquid chromatography (HPLC, FIG. 7). This is the first reported detection of $NADP^+$ utilization by LAD, although it is still considered a strongly $NAD^+$-dependent enzyme. Kinetic measurements with substrate L-arabinitol and cofactor $NAD^+$ were taken in a 5-by-5 matrix format, with substrate and cofactor concentrations varied from below their Km to 10-fold higher than their Km. The kinetic data were analyzed with a modified version of Cleland's program (Cleland, W. W. (1979) Statistical analysis of enzyme kinetic data, *Methods Enzymol* 63, 103-138.). $V_{max}$ and $K_m$ for both L-arabinitol and $NAD^+$ were obtained by fitting the data to a sequential ordered mechanism with $NAD^+$ binding first, based on the proposed mechanism for sorbitol dehydrogenase (Lindstad et al. (1992) The kinetic mechanism of sheep liver sorbitol dehydrogenase, *Eur J Biochem* 210, 641-647.)

$$v=V_{max}AB/(K_{ia}K_B+K_AB+K_BA+AB) \quad (EQ.\ 1)$$

where v is the initial velocity, $V_{max}$ is the maximum velocity, $K_A$ and $K_B$ are the Michaelis-Menten constants for NAD+ and L-arabinitol, respectively, A and B are the concentrations of NAD+ and L-arabinitol, respectively, and $K_{ia}$ is the dissociation constant for NAD+.

Table 2 displays the kinetic constants of several other sugar substrates accepted by *N. crassa* LAD. D-Arabinitol, adonitol, xylitol, D-sorbitol, and D-mannitol were all examined as alternative substrates for *N. crassa* LAD with NAD+ as the cofactor held at saturating concentration of 2 mM. Of the pentose sugar alcohols, only adonitol and xylitol acted as substrates, with $K_m$ values of 35 mM and 290 mM respectively. This pattern of substrate promiscuity is similar to those of LADs isolated from other sources.

Example 4

Temperature Dependence

Figure 2:
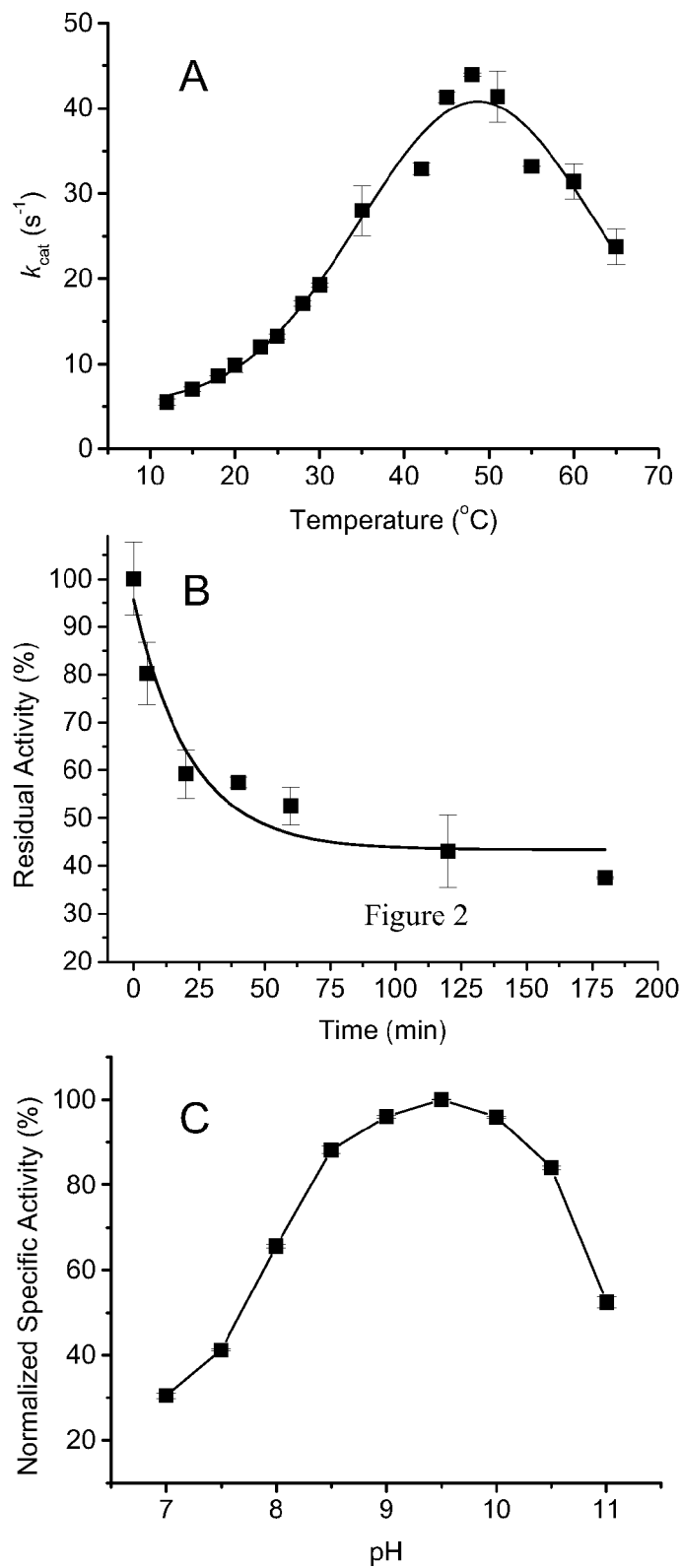
FIG. 2 demonstrates: A) $k_{cat}$ dependence on temperature. *N. crassa* LAD was assayed at different temperatures from 12 to 65° C. at saturating concentrations of 200 mM L-arabinitol and 2 mM NAD+. B) Thermal inactivation of LAD at 50° C. The heat inactivation at 50° C. was irreversible and followed first-order kinetics with a half-life of 45 min. C) pH rate profile. Saturating concentrations of 200 mM L-arabinitol and 2 mM NAD+ were used to measure the activity in a universal buffer at various pH values from 7.0 to 11.0.

The optimal temperature of activity was determined by assaying LAD activities at temperatures ranging from 12 to 65° C. The data show the optimum temperature to be between 45 and 55° C. (FIG. 2A). At higher temperatures, the enzyme inactivates rapidly, and at lowered temperatures, the rate increases with temperature according to the Arrhenius equation. Utilizing the Arrhenius equation to fit the data from 12 to 30° C., the energy of activation for L-arabinitol oxidation by *N. crassa* LAD was determined to be 49 kJ/mol. The stability for *N. crassa* LAD was relatively high, as it retained activity at room temperature for longer than one month and at 4° C. for several months. Thermal inactivation of *N. crassa* LAD was studied by incubating at 50° C. in 50 mM Tris (pH 8.0), with samples removed at various times and assayed for activity in saturating substrate conditions. FIG. 2B shows the percentage of residual activity versus incubation time, which followed a first-order exponential decay with a half-life of 45 min. Interestingly, when tested at a slightly lower temperature of 45° C., the enzyme was able to retain ~60% of its activity after 4 hr.

Example 5 pH Rate Profile

Activity was measured at pH values between 7.0 and 11.0 under saturating concentrations of NAD+ (2 mM) and L-arabinitol (200 mM) in a universal buffer (50 mM morpholineethanesulfonic acid (MES)/50 mM Tris/50 mM glycine). The pH range for *N. crassa* LAD activity was large, with >25% of the activity occurring with pH values of 7.0 to 11.0 (FIG. 2C). The pH optimum was around pH 9.5, and >60% of the activity remained in the pH span from 8.0 to 10.5.

Example 6

Determination of Mass and Quaternary Structure

Figure 4:
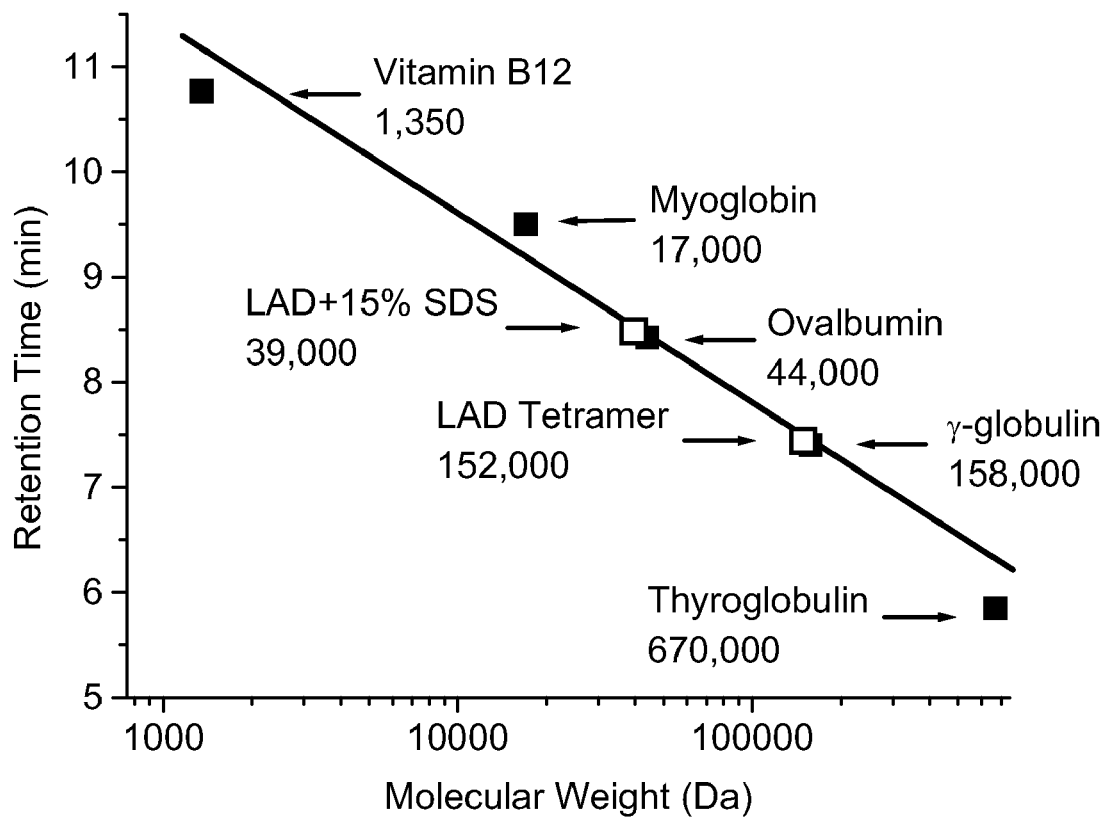
FIG. 4 shows HPLC size exclusion chromatography. A size exclusion standard was used to calibrate a Bio-Sil SEC-250, 300×7.8 mm column with a mobile phase of 0.1 M Na2HPO4, 0.15 M NaCl, 0.01 M NaN$_3$, pH 6.8 at a flow rate of 1 ml/min. The standard proteins are represented by closed squares. LAD samples (represented by open squares) with and without 15% SDS were injected separately and fitted to the standard curve.

The quaternary structure of *N. crassa* LAD was determined using an Agilent 1100 series HPLC system with a Bio-Sil SEC-250 column (300×7.8 mm) and a mobile phase of 0.1 M Na2HPO4, 0.15 M NaCl, and 0.01 M NaN3, pH 6.8. Based on the standardized retention times of a Bio-Rad molecular mass standard, the molecular mass of LAD was calculated from its retention time to be ~152 kDa (FIG. 4). Monomerization was induced in the presence of 15% SDS, causing LAD to elute as a single peak with a retention time corresponding to a molecular mass of ~39 kDa. The data indicates that the native LAD is a noncovalently linked tetramer, which is typical for fungal derived zinc-containing alcohol dehydrogenases.

Example 7

Metal Analysis

Samples of thrombin-cleaved *N. crassa* LAD were buffer exchanged with 10 mM 4-(2-hydroxyethyl)piperazine-1-ethanesulfonic acid (HEPES) buffer (pH 8.0) and lyophilized prior to submission to the Microanalytical Laboratory at the University of Illinois at Urbana-Champaign. *N. crassa* LAD was determined to contain very close to two mol of zinc/mol subunit using an inductively coupled plasma spectrophotometer (OES Optima 2000 DV, Perkin Elmer, Boston, Mass.). This is consistent with previously reported SDH and ADH enzymes containing both an active site zinc ion and a second zinc ion thought to be involved in stability. The verification of the second zinc atom also correlates well with the four conserved cysteine residues involved in structural zinc binding in homologous SDHs and XDHs.

Example 8

Cofactor Specificity

The cofactor specificity of *N. crassa* LAD was examined by HPLC. The separation of NAD+, NADP+, NADH, and NADPH was carried out using standard methods. No discernible cross-contamination of oxidized cofactors was observed. 20 μL reaction mixtures consisting of equal parts of 1 mM NAD(P)+ and 25 mM L-arabinitol in 50 mM Tris (pH 8.0) were set up, and following addition of approximately 1 μg of enzyme, the reaction was allowed to proceed for 20 min at 37° C. When NAD+ was used as the cofactor, the products were analyzed by HPLC, and a single peak (UV 340 nm) was observed that had the same retention time as authentic NADH. The same process was carried out for NADP+ as the cofactor, and a small yet detectable peak was observed with a retention time corresponding to an authentic sample of NADPH. This indicated the strong preference for NAD+ as the cofactor of N. crassa LAD.

Example 9

Homology Modeling

Figure 3:
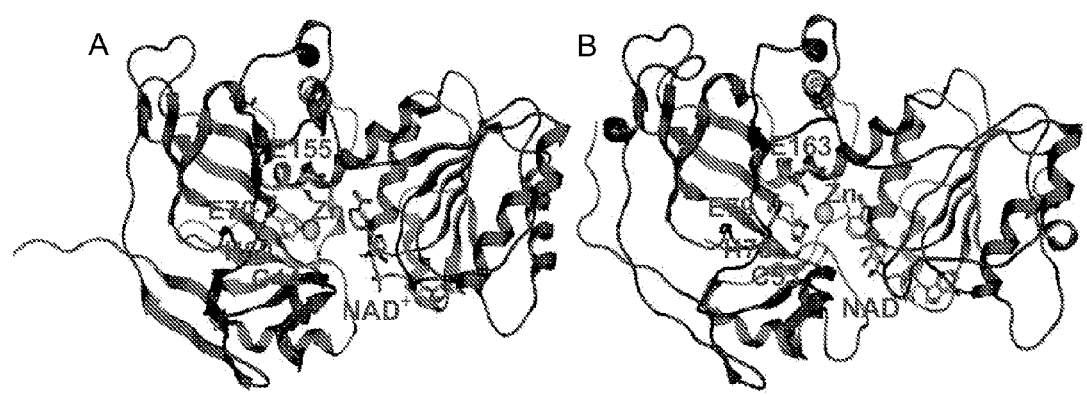
FIG. 3 shows: A) Crystal structure of human SDH with bound NAD+ and catalytic zinc ion (1PL8). B) Homology model of *N. crassa* LAD with bound NAD+ and catalytic zinc ion, built using the Insight II (Accelrys Software Inc., San Diego, Calif.) and molecular operating environment (MOE) programs. The catalytic zinc ion (Zn), four catalytic zinc binding residues, and NAD+ cofactor are colored by atom type.

Using the coordinates for NAD+-dependent human SDH (PDB accession code 1PL8) (Pauly et al. (2003) X-ray crystallographic and kinetic studies of human sorbitol dehydrogenase, Structure 11, 1071-1085) and NADP+-dependent SDH from silverleaf whitefly, Bemisia argentifolii (PDB accession code 1E3J) (Banfield et al. (2001) Crystal structure of the NADP(H)-dependent ketose reductase from Bemisia argentifolii at 2.3 Å resolution, J Mol Biol 306, 239-250), a homology model was created with Insight II software. The model was docked with NAD+ and the catalytic zinc ion, and subjected to energy minimization by using the Molecular Operating Environment (MOE) program. The model was verified for consistency with known protein folds and allowed ψ and φ angles. The resulting model was very similar to the human SDH crystal structure in overall fold and binding of coenzyme, as illustrated in FIG. 3. The only major deviation between the backbone of these two structures is the N-terminal region of amino acids 1 through 8 (FIG. 3). However, this may be due to the different conformations of the N-terminus between being in solution and forming dimerization contacts found to be present in SDH. The conserved catalytic zinc binding residues C53, H78, E79, and E163 from SDH (FIG. 3A) have similar orientations and locations in the N. crassa LAD model (FIG. 3B). When comparing proposed substrate binding residues from SDH to N. crassa LAD, the majority—S55, F127, T130, E163, R308, Y309—are strictly conserved and configured in similar orientations. However, one substrate binding residue, F59, was different from the homologous tyrosine residue in SDH, making the N. crassa LAD binding pocket slightly more hydrophobic (FIG. 6).

Example 10

F59 Mutant Kinetic Analysis

Activity assays were run for three mutants of N. crassa LAD (F59A, F59S, and F59Y) to study the effect of mutation of this active site, putative substrate binding residue homologous to tyrosine in other SDHs. All assays were carried out similar to substrate specificity profile for the wild type enzyme (described in Steady-state kinetics example), with the cofactor NAD+ held at saturating concentration of 2 mM for all assays. The mutants were still found to have activity with L-arabinitol, xylitol, and adonitol, and their kinetic parameters are displayed in Table 4. D-Sorbitol was also tested but showed no significant activity over the wild type N. crassa LAD.

TABLE 1

Kinetic parameters for N. crassa LAD[a].

| N. crassa LAD with indicated coenzyme | $K_m$ for NAD(P) (mean ± SD) (μM) | $k_{cat}$ (mean ± SD) (min$^{-1}$) | $k_{cat}/K_m$ for NAD(P) (μM$^{-1}$ min$^{-1}$) | $K_m$ for L-arabinitol (mean ± SD) (mM) |
|---|---|---|---|---|
| NAD | 174 ± 24 | 1,206 ± 54 | 6.9 | 16 ± 3 |
| NADP | — | — | $6.5 \times 10^{-7}$ | — |

[a]All assays were performed at 25° C. in 50 mM Tris, pH 8.0

TABLE 2

Kinetic parameters for N. crassa LAD with other substrates[a].

| N. crassa LAD with indicated substrate | $k_{cat}$ (mean ± SD) (min$^{-1}$) | $K_m$ (mean ± SD) (mM) | $k_{cat}/K_m$ (mM$^{-1}$ min$^{-1}$) | % Activity |
|---|---|---|---|---|
| L-Arabinitol | 1,210 ± 30 | 18 ± 2 | 67 | 100 |
| Xylitol | 970 ± 40 | 290 ± 27 | 3.3 | 4.9 |
| Adonitol | 1,080 ± 30 | 35 ± 3 | 31 | 46 |
| D-Arabinitol | — | — | ND[b] | 0 |
| D-Sorbitol | —[c] | —[c] | —[c] | 0[c] |
| D-Mannitol | — | — | ND | 0 |

[a]All assays were performed at 25° C. in 50 mM Tris, pH 8.0, at saturated NAD+ concentration
[b]ND, not detected
[c]trace activity at 2M D-sorbitol concentration, possibly due to substrate contamination

TABLE 3

Kinetic parameters of LAD from various source organisms.

| Organism (reference) | Specific activity (U/mg) | $k_{cat}$ (min$^{-1}$) | $K_{m,L-arabinitol}$ (mM) | $k_{cat}/K_{m,L-arabinitol}$ (mM$^{-1}$ min$^{-1}$) | $K_{m,NAD+}$ (μM) |
|---|---|---|---|---|---|
| N. crassa | 31 | 1,206 | 16 | 75 | 174 |
| H. jecorina | 1.6 | N/A[a] | 40 | N/A | 180 |
| H. jecorina | 0.013 | 51 | 4.5 | 11 | N/A |
| A. niger | 96 | N/A | 89 | N/A | 50 |
| A. oryzae | 0.04 | N/A | N/A | N/A | N/A |

[a]N/A, not determined

TABLE 4

Kinetic parameters of F59 mutants[a].

| Substrate | Enzyme | $k_{cat}$ (mean ± SD) (min$^{-1}$) | $K_m$ (mean ± SD) (mM) | $k_{cat}/K_m$ (mM$^{-1}$ min$^{-1}$) |
|---|---|---|---|---|
| L-Arabinitol | WT | 1,210 ± 30 | 8 ± 2 | 67 |
|  | F59Y | 840 ± 30 | 42 ± 5 | 20 |
|  | F59S | 60 ± 3 | 62 ± 9 | 0.97 |
|  | F59A | —[b] | >400 | 0.12 |
| Xylitol | WT | 970 ± 40 | 290 ± 27 | 3.3 |
|  | F59Y | —[b] | >880 | 1.2 |
|  | F59S | —[b] | >1,400 | 0.04 |
|  | F59A | —[b] | >1,850 | 0.01 |
| Adonitol | WT | 1,080 ± 30 | 35 ± 3 | 31 |
|  | F59Y | 1,420 ± 50 | 193 ± 11 | 7.4 |
|  | F59S | 120 ± 5 | 430 ± 48 | 0.28 |
|  | F59A | —[b] | >1,110 | 0.03 |

[a]All assays were performed at 25° C. in 50 mM Tris, pH 8.0.
[b]Saturation of substrate was not reached.

Materials and Methods

Strains, Plasmids and Reagents

Materials. The *Neurospora crassa* genomic sequence and LAD protein sequences were accessed from the National Center for Biotechnology Information (NCBI, www.ncbi.nlm.nih.gov). *N. crassa* 10333 was obtained from the American Type Culture Collection (ATCC). *Escherichia coli* BL21 (DE3), GST-Bind kit, biotinylated thrombin, and streptavidin agarose were purchased from Novagen (Madison, Wis.). *E. coli* μM1788 was kindly provided by William Metcalf at the University of Illinois (Urbana, Ill.). GST gene fusion expression vector pGEX-4T-3 was purchased from Amersham Biosciences (Piscataway, N.J.). SuperScript™ One-Step RT-PCR with Platinum® Taq kit was obtained from Invitrogen (Carlsbad, Calif.). Shrimp alkaline phosphatase, and PCR grade dNTPs were obtained from Roche Applied Sciences (Indianapolis, Ind.). Phusion High-Fidelity DNA Polymerase and DNA-modifying enzymes DNase I, EcoRI, NotI, and T4 DNA ligase and their appropriate buffers were purchased from New England Biolabs (NEB) (Beverly, Mass.). L-arabinitol, D-arabinitol, adonitol, xylitol, D-sorbitol, D-mannitol, ampicillin, isopropyl β-D-thiogalactopyranoside (IPTG), NADH, NADP+, and NADPH were purchased from Sigma (St. Louis, Mo.). NAD+ was a gift from Julich Fine Chemicals. Other required salts and reagents were purchased from Fisher (Pittsburgh, Pa.) or Sigma-Aldrich. The QIAprep spin plasmid mini-prep kit, QIAquick gel purification kit, RNeasy midiprep kit, and QIAquick PCR purification kit were purchased from Qiagen (Valencia, Calif.). Various oligonucleotide primers were obtained from Integrated DNA Technologies (Coralville, Iowa). SDS-PAGE gel materials, electrophoresis equipment, protein size markers, size exclusion standards (catalog number 151-1901) and Bio-Sil SEC-250, 300×7.8 mm column were purchased from Bio-Rad (Hercules, Calif.).

RT-PCR and cloning. *N. crassa* 10333 was grown on rich potato media at 30° C. for 24 h, and induced with 150 mM L-arabinose for 2 h. Since the predicted gene contained one intron, RT-PCR was utilized to isolate the processed gene. Total RNA was purified from collected cells (RNeasy purification kit, Qiagen) and treated with DNase I to remove residual genomic DNA. RT-PCR was performed using SuperScript™ One-Step RT-PCR with Platinum® Taq (Invitrogen) following the manufacturer's guidelines and suggestions for controls. Sequencing results determined at the Biotechnology Center of the University of Illinois showed the product had four silent mutations compared with the predicted sequence from the NCBI database. A control reaction consisted of the same protocol except the SuperScript™ enzyme mix was heated to 95° C. for ten minutes to thermally inactivate the reverse transcriptase enzyme and the reverse transcription thermocycler step was omitted. The primers used for the RT-PCR were: Forward 5'-GTA GCT ACG TCA GAA TTC CAT GGC TTC TAG CGC TTC C-3' (SEQ ID NO: 3) and Reverse 5'-GCT GAT TCT GCG GCC GCT TAC TCC AGA CTC TGG ATC-3' (SEQ ID NO: 4). The forward primer contained an EcoRI restriction site (shown in bold), while the reverse primer contained a NotI restriction site (shown in bold) and stop codon (underlined). The resulting RT-PCR product was isolated by a QIAquick agarose gel purification kit and amplified by an additional 20 cycles of PCR. The product was digested with EcoRI and NotI restriction enzymes and purified again by agarose gel electrophoresis. It was then ligated into pGEX-4T-3 which had been previously prepared by EcoRI and NotI digestion, dephosphorylation by shrimp alkaline phosphatase, and gel purification. The ligation mixture was precipitated with n-butanol, and resuspended in water.

The new construct was used to transform *E. coli* WM1788 by electroporation. Positive clones were selected on Luria-Bertani (LB) solid media with ampicillin at 37° C. overnight. All colonies were then removed from the plates and grown to saturation in 5 mL liquid LB from which the plasmids were purified using a QIAprep spin plasmid miniprep kit, which were used to transform *E. coli* BL21 (DE3) by heat shock. Positive clones were selected on LB solid media with ampicillin, picked individually, and assayed for LAD activity by the cell lysate assay described below. Plasmids were sequenced using the BigDye® Terminator sequencing method and an ABI PRISM 3700 sequencer (Applied Biosystems, Foster City, Calif.).

Lysate assay. *E. coli* BL21 (DE3) harboring pGEX-4T-3 derived vector were grown to maximum OD600 at 37° C. with shaking at 250 rpm. 50 μl was used to inoculate a new culture, which was grown at 37° C. with shaking at 250 rpm until an OD600 of ~0.6 was reached. The cultures were then induced with 0.3 mM IPTG and shaken at 250 rpm at 25° C. for 4 h. Cell density was then normalized to a constant OD600 and 1 mL of cells was harvested by centrifugation and lysed by resuspension in 1 mL of 1 mg/mL lysozyme/50 mM Tris (pH 8.0). The cells were frozen at −80° C. and thawed at room temperature. The resulting lysate was vortexed thoroughly and centrifuged to remove cell debris. Ten μL of the lysate was used in an assay with 200 mM L-arabinitol and 2 mM NAD+ as the substrates as described below in the Kinetics section. To determine soluble and insoluble expression, lysozyme was utilized as the lysis reagent for the induced and normalized cells following the manufacturer's recommendations and samples were subsequently analyzed by SDS-PAGE.

GST-tag removal. The GST-tag was removed by incubation with biotinylated thrombin overnight at 4° C., incubation with streptavidin agarose for 30 min at 4° C. to remove thrombin, and passing mixture through GST-Bind resin to remove GST-tag, leaving five residues (GlySerProAsnSer) (SEQ ID NO: 9) attached to the N-terminus of the *N. crassa* LAD sequence.

To determine the effect of removal of the GST-tag, the purified LAD was incubated with and without thrombin at 4° C. overnight. Complete cleavage of the 25.7 kDa tag was verified by SDS-PAGE. The specific activities of the cleaved and noncleaved samples were compared. It was determined that removal of the GST-tag enhanced activity by about 65%. Because of this significant difference in activity, the cleaved enzyme was used in all subsequent assays.

Kinetics. The data were used to calculate the kinetic constants for various substrates by fitting the Michaelis-Menten equation using Origin 5.0. *N. crassa* LAD displayed typical Michaelis-Menten type kinetics with respect to all active substrates tested except D-sorbitol. The data represent averages of assays performed in duplicate or triplicate on two separate occasions.

HPLC analysis. The enzyme (1 μg) was incubated in a mixture of buffer and 25 mM L-arabinitol with 1 mM NAD (P)+ at 37° C. for 20 min. The sample was eluted on a Zorbax 3.0×150 mm C-18 (3.5 μm) column with a UV detector (Agilent 1100 series). The eluent consisted of two components: 0.1 M KH2PO4 containing 5 mM tetrabutylammonium hydrogen sulfate (pH 5.5) (buffer A) and 100% methanol (buffer B). The most suitable gradient was an initial isocratic step for 6 min at 93% buffer A, a gradient for 5 min from 7 to 30% buffer B, and a final isocratic step for 5 min at 30% buffer B.

Homology modeling. Insight II was used to prepare the model (Insight II, version 2000; Accelrys Inc., San Diego, Calif.) and MOE (Chemical Computing Group Inc., Montreal, Canada) was used for optimization. To verify the model, the overall fold was checked using Profiles3-D (Insight II), and the allowed states for φ and ψ angles and bond distances were checked using ProStat (Insight II), both with default settings. The Profiles3-D (Insight II, default parameters) check resulted in a self-compatibility score of 139.94, which compares well to the scores of 150.53 and 145.49 for the coordinates from 1PL8 and 1E3J, respectively. The ProStat check of φ and ψ angles were determined to be 81.2% within their core expected values, comparing well to the 83.3% and 82.4% for the same analysis of PDB structures 1PL8 and 1E3J, respectively.

$$CV = \frac{\sigma_x}{<x>} \times 100\%$$

N. crassa LAD amino acid sequence:
(SEQ ID NO: 1)

```
  1 MASSASKTNI GVFTNPQHDL WISEASPSLE SVQKGEELKE GEVTVAVRST GICGSDVHFW
 61 KHGCIGPMIV ECDHVLGHES AGEVIAVHPS VKSIKVGDRV AIEPQVICNA CEPCLTGRYN
121 GCERVDFLST PPVPGLLRRY VNHPAVWCHK IGNMSYENGA MLEPLSVALA GLQRAGVRLG
181 DPVLICGAGP IGLITMLCAK AAGACPLVIT DIDEGRLKFA KEICPEVVTH KVERLSAEES
241 AKKIVESFGG IEPAVALECT GVESSIAAAI WAVKFGGKVF VIGVGKNEIQ IPFMRASVRE
301 VDLQFQYRYC NTWPRAIRLV ENGLVDLTRL VTHRFPLEDA LKAFETASDP KTGAIKVQIQ
361 SLE
```

N. crassa LAD nucleic acid sequence:
(SEQ ID NO: 2)

```
   1 atggcttcta gcgcttccaa gaccaacatt ggcgttttca ccaaccctca gcatgatctg
  61 tggatcagcg aggcctctcc ctctctcgag agcgtccaaa agggcgaaga gctgaaggaa
 121 ggcgaggtca ctgttgccgt ccgaagcaca ggcatttgcg gatccgacgt ccacttctgg
 181 aagcatggtt gcatcggccc catgatcgtc gaatgcgatc atgtcctcgg ccacgagtcg
 241 gcaggcgagg tcattgctgt ccatcccagc gtcaagagca tcaaggtcgg cgacagggtt
 301 gccattgagc ccaagtcat ctgcaatgcc tgcgagccct gcctgactgg ccgttacaac
 361 ggatgcgagc gcgttgactt cctctctacg cccctgtgc ccggcttct ccgccgctac
 421 gttaaccacc ctgccgtgtg gtgccacaaa atcggtaaca tgtcctatga aacggtgcc
 481 atgctcgagc cctttccgt ggcgctggcc ggtcttcaga gagccggtgt tcgtctgggc
 541 gaccctgtcc tcatctgtgg tgccggcccc attggtctga tcaccatgct ctgcgccaag
 601 gccgctggtg cctgccctct tgtcattacc gacattgacg aaggccgctt gaagttcgcc
 661 aaggagatct gccccgaggt cgtcacccac aaggtcgagc gcctgtcggc cgaggagtcg
 721 gccaagaaga tcgtcgagag ctttggtgga atcgagcccg cggtggctct cgagtgtact
 781 ggtgtcgaga gcagtatcgc ggctgctatc tgggccgtca gttcggcgg caaggtgttc
 841 gtcatcggcg tgggcaagaa cgagatccag attcctttca tgcgcgccag tgtgcgcgag
 901 gtcgacctgc agttccagta ccgttactgc aacacttggc ccagggccat tcgcctggtc
 961 gagaatggcc tcgttgacct caccaggctg gtgacgcacc gtttcccgtt ggaggatgcg
1021 ctcaaggcgt tcgagacggc gtcagacccc aagacgggtg ccatcaaggt gcagatccag
1081 agtctggagt aa
```

---

The invention claimed is:

1. A method of oxidizing L-arabinitol to L-xylulose, the method comprising:
   (a) obtaining a purified arabinitol dehydrogenase wherein the arabinitol dehydrogenase comprises a tetramer of a polypeptide, where the polypeptide comprises an amino acid sequence that is at least 95% similar to SEQ ID NO: 1; and
   (b) contacting a substrate containing arabinose to oxidize arabinitol with the arabinitol dehydrogenase.

2. The method of claim 1, wherein the L-xylulose is further converted to xylitol.

3. The method of claim 2, wherein the production of xylitol utilizes a phosphite dehydrogenase-based NADP regeneration system.

4. The method of claim 2, wherein the arabinitol dehydrogenase is expressed in a bacterium.

* * * * *